United States Patent [19]
Zolner

[11] Patent Number: 5,187,817
[45] Date of Patent: Feb. 23, 1993

[54] DETACHABLE WAISTBAND FOR A GARMENT

[76] Inventor: Bernard P. Zolner, 419 Heffernan Dr., Edmonton, Alberta, Canada, T6R 1W4

[21] Appl. No.: 775,859

[22] Filed: Oct. 15, 1991

[30] Foreign Application Priority Data

Oct. 24, 1990 [CA] Canada .................................. 2028431

[51] Int. Cl.$^5$ ................................................ A41B 9/00
[52] U.S. Cl. ............................................ 2/400; 2/236; 2/DIG. 7; 604/398; 604/393; 604/389
[58] Field of Search .................... 2/400, 236, DIG. 7; 604/258, 259, 260, 386, 389, 391, 393, 396, 397, 398, 400, 401, 402

[56] References Cited

U.S. PATENT DOCUMENTS

| 4,955,880 | 9/1990 | Rodriquez | 604/393 |
| 5,019,068 | 5/1991 | Perez et al. | 604/386 |

FOREIGN PATENT DOCUMENTS

| 194453 | 9/1986 | European Pat. Off. | 604/358 |
| 8402274 | 2/1985 | Netherlands | 604/358 |

Primary Examiner—Werner H. Schroeder
Assistant Examiner—Gloria Hale
Attorney, Agent, or Firm—Davis, Bujold & Streck

[57] ABSTRACT

A detachable waistband for a garment consisting of a first band which matingly engages a second band. Each band is formed of two parallel elongate strips of conjoined material. Each band has an exterior surface, a first end, a second end, and an interior surface accessible through a flap-like opening positioned intermediate the first end and the second end and extending for substantially the length of the first band. An exterior tape fastener is affixed to the exterior of each band adjacent both the first end and the second end. At least one interior tape fastener is affixed to the interior of each band. The exterior tape fasteners of the second band matingly engage the exterior tape fasteners of the first band thereby securing the first band and second band around a person's waist. The interior of the first band and the interior of the second band receive a portion of a garment. The garment is secured to the first band and the second band by the interior tape fasteners and a clamping force exerted by the two strips of material which form each band when the first band and second band are secured to a person's waist.

5 Claims, 3 Drawing Sheets

DETACHABLE WAISTBAND FOR A GARMENT

The present invention relates to a Detachable Waistband for a Garment.

BACKGROUND OF THE INVENTION

The North American consumer is becoming more environmentally conscious. At the same time Governments are being faced with rising waste disposal costs. These two forces have combined to create a demand for products which are either reusable, or if disposable are biodegradable. A major problem has been encountered in adapting a class of garments which includes diapers, and adult incontinent devices to meet this demand. Reusable washable pads have been developed, but the waistbands for holding the pads in place are generally not washable. Biodegradable disposable pads have been developed, but the waistbands for holding the pads in place are generally not biodegradable.

SUMMARY OF THE INVENTION

What is required is a Detachable Waistband for Garments such as diapers and incontinent devices.

According to the present invention there is provided a Detachable Waistband for a Garment which is comprised of a first band and a second band. The first band is formed of two parallel elongate strips of conjoined material. The first band has an exterior surface, a first end, a second end, and an interior surface accessible through a flap-like opening positioned intermediate the first end and the second end and extending for substantially the length of the first band. Exterior fastening means are affixed to the exterior of the first band adjacent both the first end and the second end. Interior fastening means are affixed to the interior of the band. The second band is formed of two parallel elongate strips of conjoined material. The second band has an exterior surface, a first end, a second end, and an interior surface accessible through a flap-like opening positioned intermediate the first end and the second end and extending for substantially the length of the second band. Exterior fastening means are affixed to the exterior of the second band adjacent both the first end and the second end. Interior fastening means are affixed to the interior of the band. The exterior fastening means of the second band matingly engage the exterior fastening means of the first band thereby securing the first band and the second band around a person's waist. The interior of the first band and the interior of the second band are adapted to receive a portion of a garment. The garment is secured to the first band and the second band by the interior fastening means and a clamping force exerted by the two strips of material which form each band when the first band and second band are secured to a person's waist.

Although a number of alternate fastening means are usable with the present invention, the Applicant prefers to use tape fasteners. Therefore, the Detachable Waistband for a Garment is comprised of a first band which matingly engages a second band. The first band is formed of two parallel elongate strips of conjoined material. The first band has an exterior surface, a first end, a second end, and an interior surface accessible through a flap-like opening positioned intermediate the first end and the second end and extending for substantially the length of the first band. An exterior tape fastener is affixed to the exterior of the first band adjacent both the first end and the second end. At least one interior tape fastener is affixed to the interior of the band. The second band is formed of two parallel elongate strips of conjoined material. The second band has an exterior surface, a first end, a second end, and an interior surface accessible through a flap-like opening positioned intermediate the first end and the second end and extending for substantially the length of the second band. An exterior tape fastener is affixed to the exterior of the second band adjacent both the first end and the second end. At least one interior tape fastener is affixed to the interior of the band. The exterior tape fasteners of the second band matingly engage the exterior tape fasteners of the first band thereby securing the first band and second band around a person's waist. The interior of the first band and the interior of the second band receive a portion of a garment. The garment is secured to the first band and the second band by the interior tape fasteners and a clamping force exerted by the two strips of material which form each band when the first band and second band are secured to a person's waist.

The invention as described permits a garment to be secured to a person's waist during use, and permits the garment to be detached from the person's waist when washing is required.

Although beneficial results may be obtained through the use of the Detachable Waistband as described, when the intended use is as a diaper it is preferable to provide some protection against leakage of urine. Even more beneficial results may be obtained in such applications by having an integrally formed impermeable outer skin integrally formed with and extending between the first band and the second band, such that the impermeable outer skin covers a person's crotch when the first band and second band are secured to a person's waist.

BRIEF DESCRIPTION OF THE DRAWINGS

These and other features of the invention will become more apparent from the following description in which reference is made to the appended drawings wherein.

DETAILED DESCRIPTION OF THE PREFERRED EMBODIMENT

Figure 1:
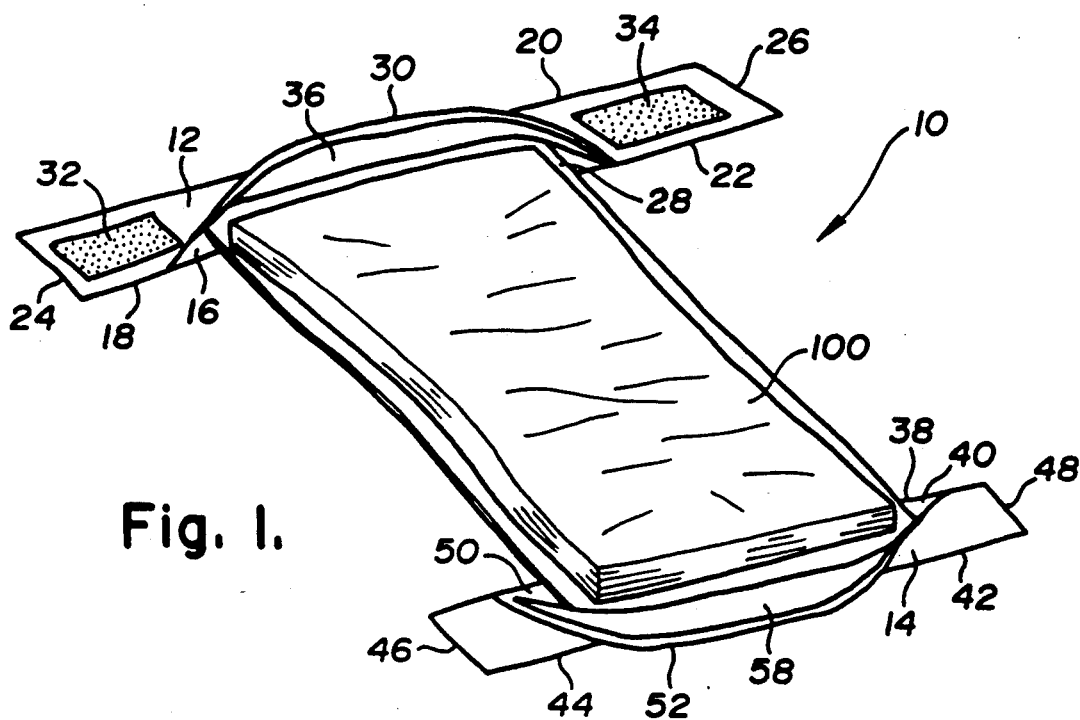
FIG. 1 is a first perspective view of a Detachable Waistband for a Garment constructed in accordance with the teachings of the invention.

The preferred embodiment, a Detachable Waistband for a Garment generally identified by reference numeral 10, will now be described with reference to FIGS. 1 through 4. An alternate embodiment will be described with reference to FIG. 5. The Garment used for the purpose of this description is a diaper, however, it must be appreciated that the Applicant is continually discovering further uses for this invention. The selection of a diaper for the purpose of illustration is not intended to limit the application of this invention to diapers.

The primary components of Detachable Waistband for a Garment 10 are a first band 12 and a second band 14. First band 12 is formed of two parallel elongate strips 16 and 18 of conjoined material. Referring to FIG. 1, it is apparent that in the illustrated embodiment strips 16 and 18 are joined along a portion of their periphery 20 and are folded at the joint. First band 12 has a first exterior surface 22, a second exterior surface 23, a first end 24, a second end 26, a first interior surface 27 and a second interior surface 28. Interior surface 28 is accessible through a flap-like opening 30 positioned intermediate first end 24 and second end 26. Opening 30 extends for substantially the entire length of first band 12. Tape fasteners 32 and 34 are used as exterior fastening means. Exterior tape fastener 32 is affixed to exterior 22 of first band 12 adjacent first end 24 and exterior tape fastener 34 is affixed adjacent second end 26. A single elongate tape fastener 36 on the second exterior surface 23 is used as interior fastening means. Interior tape fastener 36 is affixed to interior surface 28 of first band 12, and extends substantially the length of opening 30.

Second band 14 is similar in construction to first band 12. Second band 14 is formed of two parallel elongate strips 38 and 40 of conjoined material. Referring to FIG. 1, it is apparent that in the illustrated embodiment strips 38 and 40 are joined along a portion of their periphery 42 and are folded at the join. Second band has a first exterior surface 44, a second exterior surface 45, a first end 46, a second end 48, a first interior surface 49 and a second interior surface 50. Interior surface 50 is accessible through a flap-like opening 52 positioned intermediate first end 46 and second end 48. Opening 52 extends for substantially the length of second band 14. Tape fastener 54 and 56 are used as exterior fastening means. Exterior tape fastener 54 is affixed to exterior surface 44 of second band 14 adjacent first end 46 and exterior tape fastener 56 is affixed adjacent second end 48. Tape fastener 58 on the second exterior surface 45 is used as interior fastening means. Tape fastener 58 is affixed to interior surface 50 of second band 14. Tape fastener 58 extends substantially the entire length of opening 52.

Figure 2:
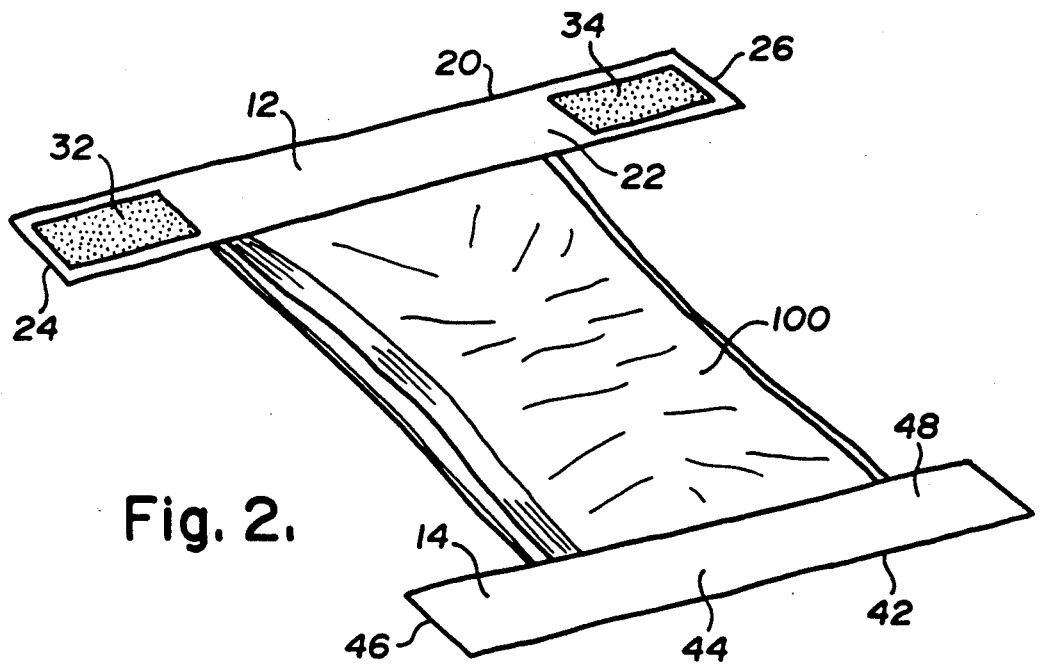
FIG. 2 is an alternate perspective view of the Detachable Waistband for a Garment illustrated in FIG. 1.
Figure 3:
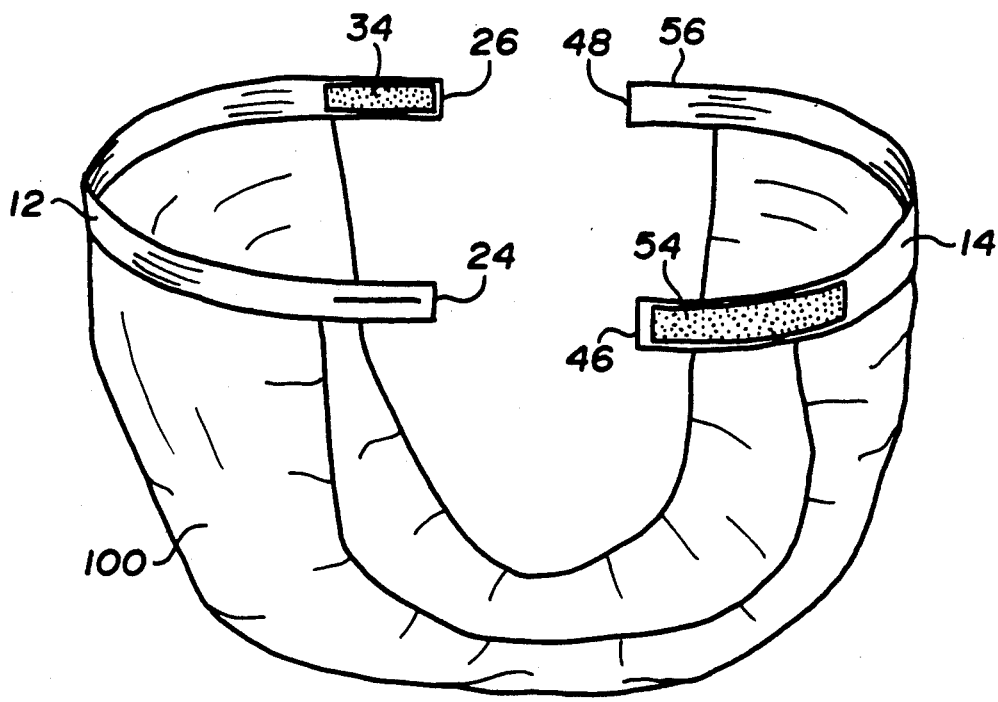
FIG. 3 is a first perspective view of the Detachable Waistband for a Garment, with Garment attached.
Figure 4:
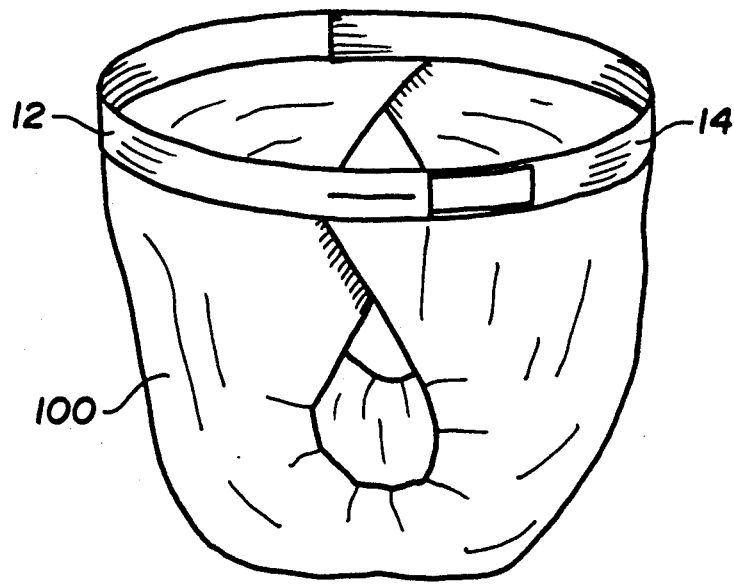
FIG. 4 is an alternate perspective view of the Detachable Waistband for a Garment illustrated in FIG. 3.

The use and operation of Detachable Waistband for a Garment 10 will now be described with reference to FIGS. 1 through 4. Referring to FIGS. 1 and 2, interior surface 28 of first band 12 and interior surface 50 of second band 14 are adapted to receive a portion of a garment, identified for the purpose of this description by reference numeral 100. For the purpose of this description a diaper pad is used as the garment. Garment 100 does not form part of the present invention. Garment 100 is secured to a first band 12 and second band 14 by interior tape fasteners 36 and 58, respectively. Referring to FIGS. 3 and 4, exterior tape fasteners 54 and 56 of second band 14 matingly engage exterior tape fasteners 32 and 34 of first band 12 thereby securing first band 12 and second band 14 together. In FIG. 4 first band 12 and second band 14 are illustrated in the position they would assume when placed around a person's waist. A clamping force is exerted by strips of material 16 and 18 which form first band 12 and by strips of material 38 and 40 which form second band 14 upon garment 100 when first band 12 and second band 14 are secured to a person's waist.

Figure 5:
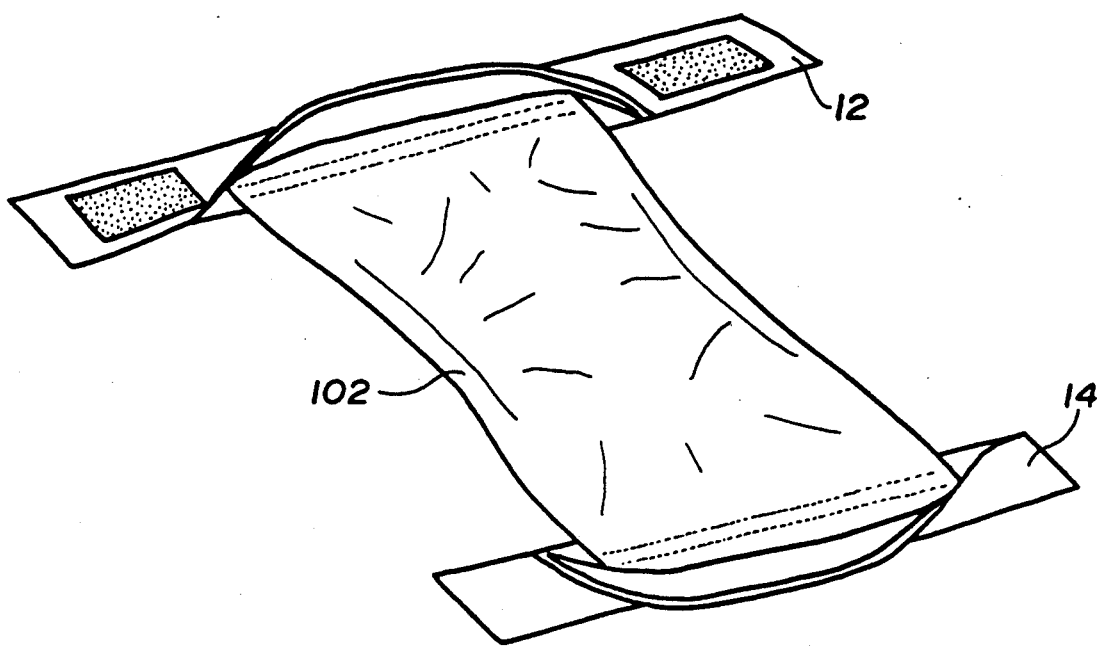
FIG. 5 is an alternate embodiment constructed in accordance with the teachings of the invention.

The use and construction of the alternate embodiment illustrated in FIG. 5 is the same as that for the preferred embodiment. The only difference is the addition of an integrally formed impermeable outer skin 102 extending between first band 12 and second band 14. Impermeable outer skin 102 covers a person's crotch (not shown) when first band 12 and second band 14 are secured to a person's waist. Impermeable outer skin 102 is desirable when the intended use is as a diaper, as it provides some protection against leakage of urine. In such applications garment 100 is secured to first band 12 and second band 14 as previously described, serving as a washable liner.

It will be apparent to one skilled in the art that the present invention permits a garment to be secured to a person's waist during use, and permits the garment to be detached from the person's waist when washing is required. It will also be apparent to one skilled in the art that the invention has wide application, and is not limited in scope to the use for diapers and the like. It will finally be apparent that modifications may be made to the illustrated embodiments without departing from the spirit and scope of the invention. In particular, there are a wide variety of interior fastening means and exterior fastening means which can be used to duplicate the Applicant's successful result.

The embodiments of the invention in which an exclusive property or privilege is claimed are defined as follows:

1. A detachable waistband for a garment, comprising:
a) a first band formed of two parallel elongate strips of conjoined material, the first band having a first exterior surface, a second exterior surface, a first end, a second end, and a pair of opposed interior surfaces accessible through a flap-like opening positioned intermediate the first end and the second end and extending for substantially the length of the first band, exterior fastening means being affixed to one of the exterior surfaces of the first band adjacent both the first end and the second end, interior fastening means being affixed to one of the interior surfaces of the band;
b) a second band formed of two parallel elongate strips of conjoined material, the second band having a first exterior surface, a second exterior surface, a first end, a second end, and a pair of opposed interior surfaces accessible through a flap-like opening positioned intermediate the first end and the second end and extending for substantially the length of the second band, exterior fastening means being affixed to one of the exterior surfaces of the second band adjacent both the first end and the second end, interior fastening means being affixed to one of the interior surfaces of the band, exterior fastening means of the second band matingly engaging the exterior fastening means of the first band thereby securing the first band and second band around a person's waist, the interior surfaces of the first band and the interior surfaces of the second band being arranged to receive a portion of a garment, such that the garment is secured to the first band and the second band by the interior fastening means and a clamping force exerted by the two strips of material which form each band when the first band and second band are secured to a person's waist.

2. A detachable waistband for a garment, comprising:
a) a first band formed of two parallel elongate strips of conjoined material, the first band having a first exterior surface, a second exterior surface, a first end, a second end, and a pair of opposed interior surfaces accessible through a flap-like opening positioned intermediate the first end and the second end and extending for substantially the length of the first band, an interior tape fastener being affixed to the first exterior surface of the first band adjacent both the first end and the second end, at least one interior tape fastener being affixed to one of the interior surfaces of the band;

b) a second band formed by two parallel elongate strips of conjoined material, the second band having a first exterior surface, a second exterior surface, a first end, a second end, and a pair of opposed interior surfaces accessible through a flap-like opening positioned intermediate the first end and the second end and extending for substantially the length of the second band, an exterior tape fastener being affixed to the second exterior surface of the second band adjacent both the first end and the second end, at least one interior tape fastener being affixed to one of the interior surfaces of the band, the exterior tape fasteners of the second band matingly engaging the exterior tape fasteners of the first band thereby securing the first band and second band around a person's waist, the interior surfaces of the first band and the interior surfaces of the second band being arranged to receive a portion of a garment, such that the garment is secured to the first band and the second band by the interior tape fasteners and a clamping force exerted by the two strips of material which form each band when the first band and second band are secured to a person's waist.

3. A Detachable Waistband for a Garment as defined in claim 1, an integrally formed impermeable outer skin being integrally formed with and extending between the first band and the second band, such that the impermeable outer skin covers a person's crotch when the first band and second band are secured to a person's waist.

4. A detachable waistband for a garment, comprising:

a) a first band formed of two parallel elongate strips of conjoined material, the first band having a first exterior surface, a second exterior surface, a first end, a second end, and a pair of opposed interior surfaces accessible through a flap-like opening positioned intermediate the first end and the second end and extending for substantially the length of the first band, exterior fastening means being affixed to one of the exterior surfaces of the first band adjacent both the first end and the second end;

b) a second band formed of two parallel elongate strips of conjoined material, the second band having a first exterior surface, a second exterior surface, a first end, a second end, and a pair of opposed interior surfaces accessible through a flap-like opening positioned intermediate the first end and the second end and extending for substantially the length of the second band, exterior fastening means being affixed to one of the exterior surfaces of the second band adjacent both the first end and the second end, exterior fastening means of the second band matingly engaging the exterior fastening means of the first band thereby securing the first band and second band around a person's waist, the interior surfaces of the first band and the interior surfaces of the second band being arranged to receive a portion of a garment, such that the garment is secured to the first band and the second band by the interior fastening means and a clamping force exerted by the two strips of material which form each band when the first band and second band are secured to a person's waist.

5. A detachable waistband for a garment as defined in claim 4, an integrally formed impermeable outer skin being integrally formed with and extending between the first band and the second band, such that the impermeable outer skin covers a person's crotch when the first band and second band are secured to a person's waist.

* * * * *

UNITED STATES PATENT AND TRADEMARK OFFICE
CERTIFICATE OF CORRECTION

PATENT NO. : 5,187,817
DATED : February 23, 1993
INVENTOR(S) : Bernard Peter ZOLNER It is certified that error appears in the above-identified patent and that said Letters Patent is hereby corrected as shown below:

Column 4, line 67 replace "interior" with --exterior--.

Signed and Sealed this

Twenty-third Day of November, 1993

Attest:

BRUCE LEHMAN

Attesting Officer  Commissioner of Patents and Trademarks